(12) United States Patent
dos Santos Cristiano et al.

(10) Patent No.: US 6,384,264 B1
(45) Date of Patent: May 7, 2002

(54) PHOTOACTIVE MATERIALS APPLICABLE TO IMAGING SYSTEMS

(75) Inventors: Maria de Lurdes dos Santos Cristiano, Faro (PT); John Kynaston Davies, Leeds (GB); Sharon Dowd, Liverpool (GB); Robert Alexander Walker Johnstone, Wirral (GB); Michael John Pratt, Ilkley (GB); John Robert Wade, Leeds (GB)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 09/691,860

(22) Filed: Oct. 18, 2000

Related U.S. Application Data

(62) Division of application No. 09/218,079, filed on Dec. 22, 1998, now Pat. No. 6,171,756.

(30) Foreign Application Priority Data

Dec. 24, 1997 (GB) .............................................. 9727186

(51) Int. Cl.[7] ............................................. C07C 269/02
(52) U.S. Cl. ......................................... 560/22; 560/163
(58) Field of Search .................................... 560/22, 163

(56) References Cited

U.S. PATENT DOCUMENTS 5,820,944 A * 10/1998 Harkness et al. ........... 427/510

OTHER PUBLICATIONS

Tetrahedron Letters, 29(1), 1988, pp. 65–68.*

* cited by examiner

*Primary Examiner*—Brian J. Davis
(74) *Attorney, Agent, or Firm*—Breiner & Breiner, L.L.C.

(57) ABSTRACT

Organic photoprecursors of amines are provided for use in photosensitive imaging systems, finding particular application in the preparation of lithographic printing plates. Said photoprecursors generate free amines on exposure to long wavelength UV or visible radiation, have high solubility in organic solvents, and include photolabile 2-nitrobenzyl functional groups. Methods for the synthesis of the photoprecursors are described, and the use of the said photoprecursors for the production of printing plates using both positive working and negative working techniques are discussed.

10 Claims, No Drawings

PHOTOACTIVE MATERIALS APPLICABLE TO IMAGING SYSTEMS

This is a division of application Ser. No. 09/218,079 filed Dec. 22, 1998 now U.S. Pat. No. 6,171,756.

FIELD OF THE INVENTION

This invention relates to photoactive materials which are useful in imaging systems. More particularly, the invention is concerned with materials which are capable of generating free bases on interaction with radiation.

Photogeneration of active species has proved to be extremely important in many areas and photolabile protecting groups have been used widely in organic and bio-organic synthesis. Photocurable polymers have found many applications in coating technology and photoresists are important in fabrication of microelectronic devices. Although some such applications involve very short wavelength ultraviolet irradiation or even electron beams, most commercial systems use ultraviolet or visible light sources because of their ease of use for low cost.

In lithography, compounds that produce radicals and/or acids on photolysis have been used extensively as photoinitiators in positive and negative working imaging systems. Thus, irradiation with light may be used to effect polymer formation, or polymer side-chain modification. In situ generation of acid is used as a means of inducing polymerisation of monomers or oligomers or to effect cross-linking, and both of these processes normally lead to less soluble materials. Despite the possibilities for application of base catalysts, the use of photogenerated bases in imaging systems has attracted little attention. In most photochemical reactions that liberate a base (usually an amine), it is trapped in solution in its largely neutral protonated form so that such processes are of little utility with systems that require base catalysts. Major exceptions lie in deep-UV irradiation of transition metal-amine complexes with negative photoresist systems, which photogenerate ammonia in a quantum efficient process and short wavelength irradiation of $\alpha,\alpha$-dimethyl-3,5-dimethoxybenzyloxy carboxamides, which yield amines. Thus, compared with acid-release systems, there are few general base-release agents useful for short- and long-wavelength lithographic applications.

The present invention seeks to provide organic photoprecursors of amines which may find application in lithographic printing plates or photoresist systems, and methods for the production of said photoprecursors.

Advantageously, said photoprecursors may be caused to photochemically generate free amines via interaction with long wavelength UV or visible radiation and may then serve to cause a change in the dissolution properties of a coating composition in developer solutions, thereby effecting differences in solubility properties in exposed and unexposed regions and facilitating image formation. Alternatively, changes in colour between irradiated and non-irradiated areas may be caused to occur with the incorporation of base-sensitive dyes into the coatings, thereby allowing for ready distinction between image and non-image areas.

The conception of generation of amines by irradiation of systems with light is well known from the synthesis of peptides or nucleotides, wherein photolabile protecting groups are used until the final steps of the synthesis in order to protect the amine. Cleavage of the masking groups then allows the amine to be regenerated, preferably by irradiation with visible or long-wavelength UV light, in a process having high quantum efficiency.

An especially suitable photolabile group for systems of this type is the 2-nitrobenzyl group. Particular attention has focused on 2-nitrobenzyl compounds, in which the benzylic group carries at least one $\alpha$-hydrogen atom; these derivatives are known to undergo photoinduced intermolecular oxygen transfer with reduction of the nitro group to a nitroso group and simultaneous oxidation of the benzylic side chain. This process is initiated by photoinduced hydrogen abstraction by an ortho-nitro group from the nearby benzylic carbon functionality, followed by transfer of a hydroxyl group from the nitro group back on to the carbon atom from which the hydrogen was abstracted.

Several derivatives of this type have been reported in the prior art. Photosensitive polymers which are used to form resist patterns, and which contain o-nitro benzyl oxy units are disclosed in unexamined Japanese Patent Specification No. 63-146032 and unexamined Japanese Patent Specification No. 63-247749 describes a range of o-nitro aryl oxy and o-nitro hetaryl oxy unit-containing polymers useful in the photosensitive layers of offset printing plates.

Subsequently, unexamined Japanese Patent Specifications Nos 03-131626 and 03-141357 have disclosed photosensitive amphipathic high molecular weight compounds which comprise polyesters or polyester acids or their esters which are prepared from tetracarboxylic acid dianhydrides and diols containing o-nitrobenzyl groups, the acid dianhydride optionally being reacted with an alcohol and converted to an acid halide prior to reaction with the diol. The compounds are utilised in light sensitive ultra-thin films.

More recently, improved quantum efficiency of photoreaction has been reported when employing dinitrobenzyl derivatives as precursors for photoreactive compounds as disclosed, for example, in U.S. Pat. Nos. 5,449,834 and 5,600,035. Thus, various 2,5- and, most preferably, 2,6-dinitro-benzyl derivatives have been used as monomers for the preparation of photosensitive polymers, having especially enhanced sensitivity at longer wavelengths. Particular use has been made of dichlorodinitro compounds and dinitrodiols in this regard, with 2,6-dinitro-4-methoxycarbonylbenzaldehyde having found particular application. Various polyurethanes, polysulphides, polyesters, and polyamines have been prepared from these precursors.

Unfortunately, however, whilst a high degree of photosensitivity is achieved with these products, their synthesis is not a trivial matter and the materials are only obtained with difficulty. Additionally, the compounds, like many polynitro derivatives, suffer from poor solubility in a range of common organic solvents, such as hydrocarbons, alcohols, ketones and the like.

It is, therefore, an object of the present invention to provide highly photosensitive compounds, capable of efficient photoreaction allowing for the production of basic materials during said photoreaction, wherein the photosensitive compounds and corresponding precursors may be simply and efficiently prepared by means of standard synthetic techniques.

It is a further object of the present invention to provide highly photosensitive compounds as hereinbefore described, having a high level of solubility in a range of common organic solvents.

The present inventors have found that the general principles discussed may be applied to urethanes having the general structural formula I.

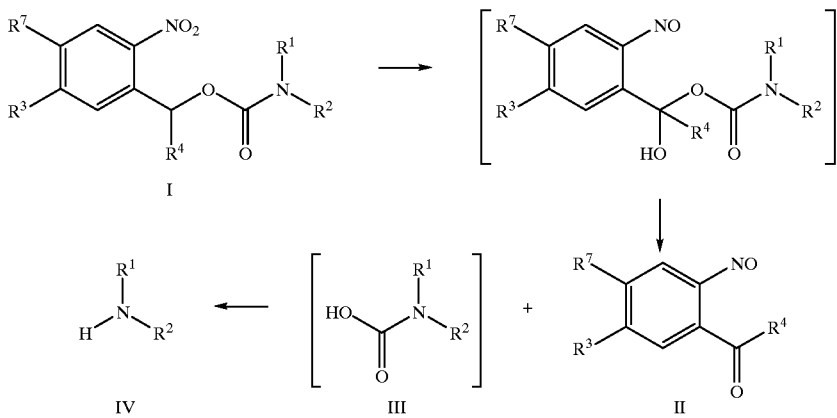

I

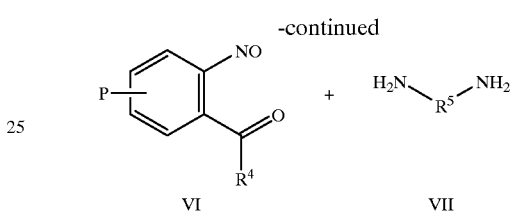

IV      III      II $R^1$, $R^2$ = H or optionally substituted alkyl, aryl or aralkyl;
$R^3$, $R^7$ = H or substituent
$R^4$ = H or lower alkyl.

Thus, on irradiation, the compound I undergoes light induced internal rearrangement to produce nitroso derivative II and carbamic acid III. Due to the instability of the acid III, its formation is followed rapidly by spontaneous release of carbon dioxide to give the free amine IV. Hence, suitable urethanes I are photoprecursors of amines and may be used as photoactive compounds for photoimaging.

Furthermore, it has also been found that polymeric derivatives, including for example polycarbonates or polycarbamates which include the 2-nitrobenzyl functionality will undergo similar light-induced degradation. Thus, photolysis of a polycarbamate results not only in polymer degradation by cleavage at the carbamate linkages, but also in functional changes on the resulting fragments which contain terminal basic amino groups, whereas the original polymer is neutral. Therefore, such polymers may be used to provide a positive-working photoimaging system wherein the irradiated areas of a coating may be washed away with an aqueous acidic developer, thereby producing a three-dimensional relief image, for example via the degradation of a polymer V to a nitroso derivative VI and a diamine VII. It has also been found that these polymers are of value in the production of negative-working photoimaging systems, since the breakdown products—containing basic amino groups—which are present in the irradiated areas of the coating are insoluble in aqueous alkaline developers containing a small amount of solvent, whereas such developers cause dissolution of the unirradiated areas due to the presence of polymers which include urethane groups carrying acidic protons; such polymers thereby confer solubility in aqueous alkaline solutions, particularly in the presence of small amounts of solvents which enhance the solubility of the polymers.

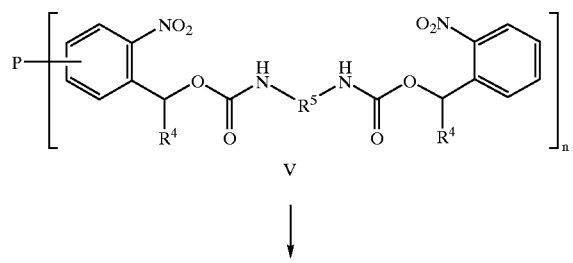

V

-continued

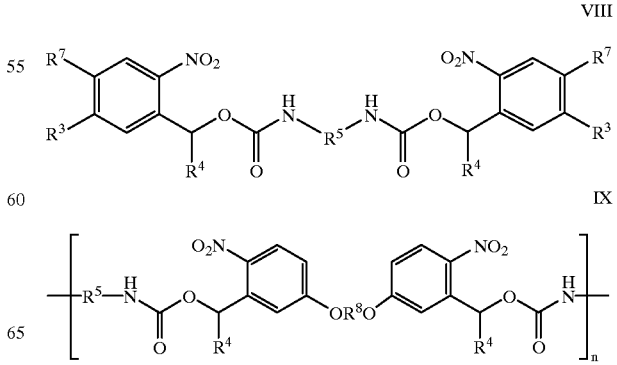

VI      VII

P = direct bond or linking group;
$R^4$ = H or lower alkyl;
$R^5$ = optionally substituted alkylene, arylene or aralkylene;
$n$ = integer.

A first aspect of the present invention provides organic photoprecursors of amines for use in photosensitive imaging systems, said photoprecursors generating free amines on exposure to long wavelength UV or visible radiation and having high solubility in organic solvents, and said photoprecursors including photolabile 2-nitrobenzyl functional groups.

Said photoprecursors are especially useful in photosensitive systems used for the production of lithographic printing plates.

Preferably, said photoprecursors including photolabile 2-nitrobenzyl functional groups comprise 2-nitrobenzyl urethane derivatives of the formulae I or VIII or derived polyurethanes of the formulae V, IX and X. Derivatives I are prepared by employing monoisocyanates in the synthesis, whilst diisocyanates are used for the preparation of compounds, V, VIII, IX and X.

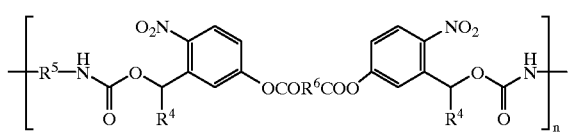

$R^4$ = H or lower alkyl;
$R^5$, $R^6$ = optionally substituted alkylene, arylene or aralkylene;
$n$ = integer.

Particularly favourable results have been achieved with 2-nitrobenzyl urethane derivatives wherein the benzyl group is substituted with an alkyl group, preferably with a methyl group. Optionally, the aryl ring may be further substituted, most preferably with methoxy groups, or other groups capable of producing bathochromic shifts in the wavelength of maximum absorption of the parent (unsubstituted) compound.

It has been found that optimum sensitivity for compounds which are intended for use in deep UV photolithography, at around 250 nm, is achieved when the 2-nitrobenzyl ring carries no further ring substituents. On the other hand, bathochromic shifts of the main absorption band of the order of 100 nm may be achieved by the introduction of electron donating substituents, preferably methoxy groups, into the 2-nitrobenzyl ring. Consequently, derivatives which are especially suitable for near UV/visible photolithographic applications may be obtained.

A second aspect of the present invention provides a method of preparing a lithographic printing plate comprising the steps of:

a) providing a lithographic printing plate precursor comprising a substitute and a photosensitive coating comprising an organic photoprecursor according to the first aspect of the invention;
b) imagewise exposing the printing plate precursor to radiation; and
c) developing the plate.

A lithographic printing plate precursor may be conveniently obtained by dissolving an organic photoprecursor according to the first aspect of the invention in any of a range of common organic solvents and coating the solution on to a suitable lithographic substrate. Potential coating solvents typically include aromatic hydrocarbons such as toluene, alcohols, for example ethanol or isoproponal, and ketones such as acetone or methyl ethyl ketone, or mixtures of any of these solvents.

Optionally, the photosensitive coating layer may also include additional lithographically useful materials, for example: support resins, preferably those containing groups capable of conferring solubility or swellability in aqueous solutions; colour change dyes, including especially pH sensitive colour change dyes; shading dyes; pigments; sensitisers; stabilisers; surfactants and other suitable materials.

The material used for the substrate depends upon the specific purpose for which the image is to be used and may be, for example, a metal, paper or plastics material. In the case where the image is to be used as a printing image, the substrate is preferably aluminium, most preferably electrochemically roughened aluminium which includes a surface layer of anodic aluminium oxide.

The resulting printing plate precursor is imagewise exposed to long wavelength UV or visible radiation, most conveniently by means of, for example, a Berkey-Ascor printing down frame. Consequent photodegradation of the precursor in the radiation struck areas allows for the generation of free amine in these areas, thereby rendering the exposed coating suitable in aqueous acidic media. These areas may then be developed away by application of a suitable acidic developer, leaving a positive image on the plate which may be used for the production of copies on a printing press.

Alternatively, as previously observed, it is possible to obtain a negative image by judicious selection of the developing solution to make appropriate use of the solubility differential which exists between the exposed and unexposed areas of the coating. Thus, by incorporation of a small amount of a suitable solvent, typically benzyl alcohol, in an aqueous alkaline solution containing an appropriate anionic surfactant, for example a sulphonated naphthalic acid derivative, a developer is obtained which may be used for the preparation of a printing plate from a photographic negative, the plate subsequently finding use for the production of copies on a printing press.

Such so called image-reversal techniques, whereby both positive- and negative-working images may be produced from the same printing plate precursor, are already known from the prior art and are disclosed, for example, in GB-B-2188448. However, the teachings of the earlier art inevitably require the use of additional steps, such as a blanket exposure of the plate or a further baking procedure, during the platemaking process. By application of the present invention such additional stages of platemaking can be eliminated thereby leading to savings in terms of both time and cost, with a consequent improvement in efficiency.

In terms of the press performance of lithographic printing plates including photoprecursors according to the first aspect of the present invention, it is found that enhanced performance, in terms of greater durability, is achieved by the use of polymeric derivatives as hereinbefore described. Particularly favourable results may be obtained by the use of polymeric photoprecursors in combination with support resins.

A further aspect of the present invention, provides a method of preparing organic photoprecursors of primary amines according to the first aspect of the invention, said method comprising the steps of:

(i) nitrating an aromatic aldehyde or ketone XI to provide the o-nitro derivative XII;
(ii) reducing said o-nitro derivative XII to the corresponding alcohol XIII; and
(iii) reacting said alcohol XIII with mono- or di-isocyanates to provide 2-nitrobenzyl urethane derivatives I ($R^2$=H) or VIII.

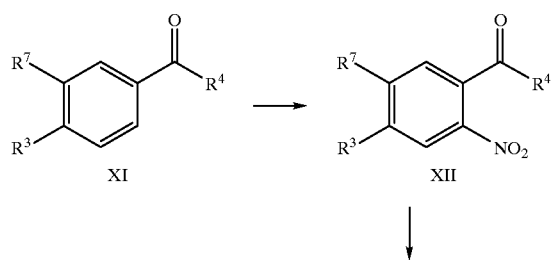

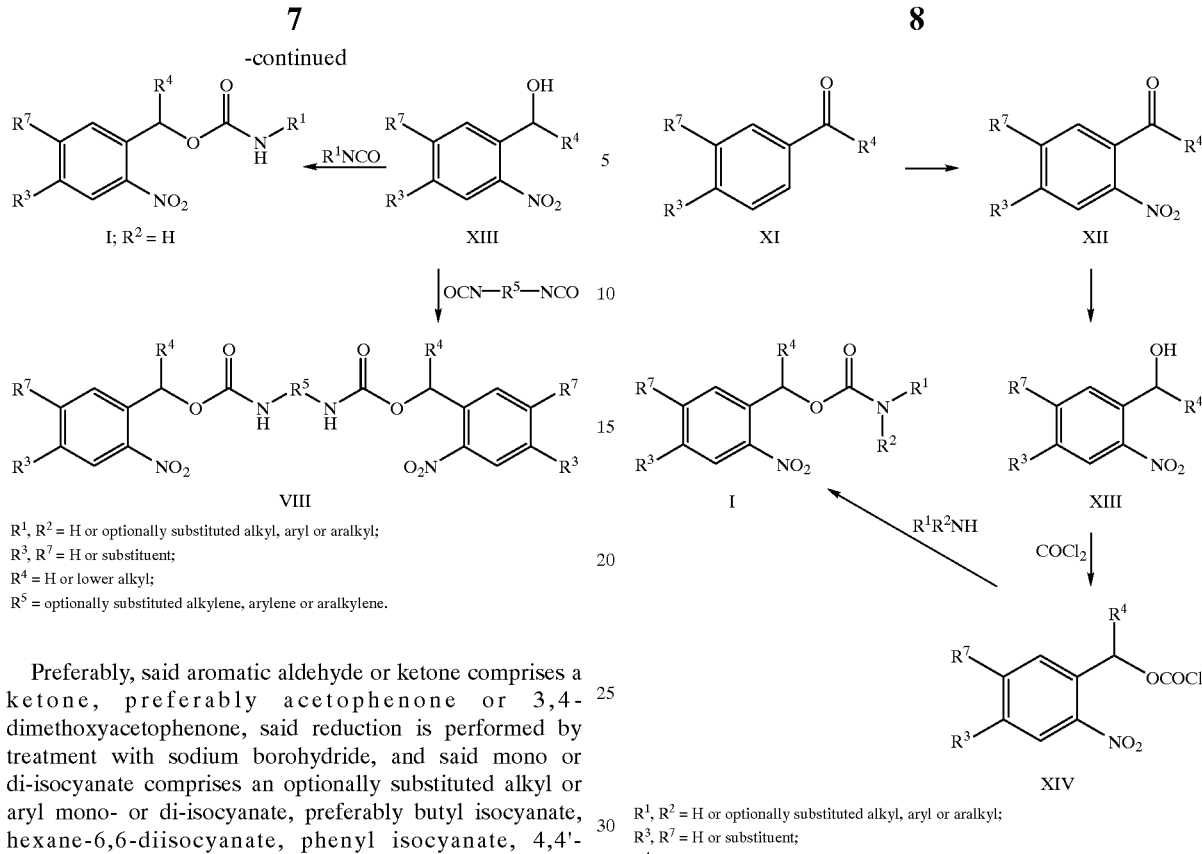

Preferably, said aromatic aldehyde or ketone comprises a ketone, preferably acetophenone or 3,4-dimethoxyacetophenone, said reduction is performed by treatment with sodium borohydride, and said mono or di-isocyanate comprises an optionally substituted alkyl or aryl mono- or di-isocyanate, preferably butyl isocyanate, hexane-6,6-diisocyanate, phenyl isocyanate, 4,4'-diisocyanatodiphenylmethane or 4-nitrophenylisocyanate.

The reaction of said alcohol with mono- or di-isocyanates is most advantageously carried out at elevated temperatures, preferably 30–150° C., most preferably 50–120° C., in an aromatic hydrocarbon solvent such as toluene, under an inert atmosphere. High yields are generally achieved.

Polymeric derivatives may be prepared by employing bisaldehydes or bisketones which, by reaction of the derived nitro-alcohols with diisocyanates, allow for the preparation of bits (2-nitrobenzyl urethane) derivatives which then serve as precursors to polymers. Alternatively, polymers may also be prepared from the reaction of diisocyanates with 2-nitroalcohols containing further active hydrogen-containing groups, such as hydroxy or mercapto groups, for example 5-hydroxy-2-nitrobenzyl alcohol.

Said 2-nitrobenzyl urethane derivatives contain N-substituted amino groups, which may be further substituted by alkylation of the amino group using an alkyl halide, preferably methyl iodide, in order to provide organic photoprecursors of secondary amines. Said alkylation is most conveniently carried out in an efficient polar solvent, such as dimethylformamide, in the presence of a reductive catalyst, typically sodium hydride.

A still further aspect of the present invention provides a method of preparing organic photoprecursors of secondary amines according to the first aspect of the invention, said method comprising the steps of:

(i) nitrating an aromatic aldehyde or ketone XI to provide the o-nitro derivative XII;

(ii) reducing said o-nitro derivative XII to the corresponding alcohol XIII;

(iii) reacting said alcohol XIII with carbonyl chloride to provide the corresponding chlorocarbonate XIV; and (iv) condensing said chlorocarbonate XIV with a secondary amine.

Preferably, said aromatic aldehyde or ketone comprises a ketone, preferably acetophenone or 3,4-dimethoxyacetophenone, said reduction is performed by treatment with sodium borohydride, and said secondary amine comprises an optionally substituted dialkylamine, preferably a lower dialkylamine such as diethylamine or disopropylamine.

The successful preparation of the chlorocarbonates requires the presence of a constant large excess of carbonyl chloride (phosgene) in order to suppress formation of the corresponding bis-carbonate derivative. Under such conditions, yields in excess of 90% are achievable.

The inventors have demonstrated the usefulness of the products of the present invention as photoprecursors for amines by studying their behaviour in solution and in solid film. Thus, samples of photoprecursors, dissolved in suitable solvents such as benzene, methanol or tetrahydrofuran (THF), and deaerated by the passage of a stream of nitrogen, were irradiated with lamps having a spectral output forming a continuum from the deep UV to the near IR region, and having strong emission lines at 365, 405 and 436 nm; Oriel 500W Hg(Xe) arc lamps were particularly suitable for this purpose. Analysis of the solution over time during irradiation, by means of thin layer chromatography and gas chromatography-mass spectrometry (GC/MS), allowed for the photolysis process to be followed in terms of decrease of photoprecursor and appearance and increase in quantity of new materials, including nitroso compound and, most particularly, amine. It was noted, however, that the use of THF as solvent resulted in the formation of pyrrole derivatives on irradiation due to reaction between the solvent and the liberated amines; this phenomenon was not observed when employing other solvents.

In a similar fashion, irradiation of a photoprecursor on a filter paper in the presence of pH sensitive dye or dye indicator, such as bromothymol blue (pH range 6.0–7.6) was achieved by pouring solutions of both materials on to the paper and irradiating with the aforesaid light source. A yellow to blue colour change was indicative of the release of a base. Alternatively, the same effect was achieved by using an anodised aluminium plate, rather than a filter paper, as the substrate.

The above invention will now be illustrated, without limitation by reference to the following experiments:

Preparation of intermediate compounds
2-Nitro-4,5-dimethoxyacetophenone (XII; $R^3$=OCH$_3$, $R^4$=CH$_3$)

3,4-dimethoxyacetophenone (15 g; 83.2 mmol) was added in small amounts to well stirred, ice-cooled nitric acid (sp gr 1.42; 90 ml) over a period of 1 hr. The final mixture was stirred for one further hour and then poured onto 400 g of crushed ice. When the ice had melted the resulting yellow solid was filtered off, air-dried and recrystallized from ethanol (9.5 g; 50.7% yield).

1-(2-Nitrophenyl)ethanol (XIII; $R^3$=H, $R^4$=CH$_3$)

Sodium borohydride (1.2 g; 32 mmol) was added in small portions over a period of 30 minutes to a stirred solution of 2-nitroacetophenone (10 g; 60.55 mmol) in dry methanol (100 ml). The resulting mixture was stirred at room temperature for a further 4 hr, after which TLC indicated complete absence of starting material. Ice-water (50 ml) was added to the reaction mixture and the required organic alcohol was extracted with chloroform (3×100 ml) to afford a light yellow oil (10.87 g). Purification by flash chromatography on silica, eluting with dichlormethane, gave 1-(2-nitrophenyl)ethanol as a light yellow oil (10.02 g; 98% yield).

1-(4,5-Dimethoxy-2-nitrophenyl) ethanol (XIII; $R^3$=OCH$_3$; $R^4$=CH$_3$)

Sodium borohydride (0.5 g; 13.2 mmol) was added in small portions to a stirred mixture of 2-nitro-4,5-dimethoxyacetophenone (5 g; 22.2 mmol) in dry methanol (50 ml), over a period of 10 min. The mixture was stirred overnight at room temperature and then ice-water (50 ml) was added to the reaction mixture; the required alcohol was extracted with chloroform (3×50 ml) to give the product as light yellow crystals (from ethanol; 4.2 g; 84% yield); mp 107–108° C.

1-(2-Nitrophenyl)-1-ethoxycarbonyl chloride (XIV; $R^3$=H, $R^4$=CH$_3$)

Dry dichloromethane (30 ml) was cooled in an ice-bath and phosgene was bubbled into it for 30 min, after which a solution of 1-(2-nitrophenyl)ethanol (2 g, 12 mmol) and triethylamine (1.2 g; 12 mmol) in dichloromethane (10 ml) was added over a period of 10 min. The final mixture was stirred for a further 20 min, after which TLC indicated that no starting material was present. The mixture was purged with nitrogen to remove excess of phosgene and the precipitated triethylammonium chloride was filtered off. The filtrate was evaporated to dryness under vacuum at a bath temperature below 40° C. to give a yellow oil, which was purified by flash chromatography on silica, eluting with dichloromethane to afford the required carbonyl chloride as an oil; this was used immediately for the preparation of the required carbamate (2.53 g; 92% yield).

Preparation of photoprecursors of amines

Photoprecursors of amines were prepared according to the scheme shown in Table 1, and wavelengths of maximum absorption (λmax) were measured in each case.

TABLE 1

| I | $R^1$ | $R^2$ | $R^3$ | $R^4$ | λmax (nm) |
|---|---|---|---|---|---|
| a | H | C$_6$H$_5$ | H | CH$_3$ | 206, 236, 254 |
| b | CH$_3$ | C$_6$H$_5$ | H | CH$_3$ | 207, 238, 255 |
| c | H | CH$_3$(CH$_2$)3 | H | CH$_3$ | 208, 256 |
| d | C$_2$H$_5$ | C$_2$H$_5$ | H | CH$_3$ | 208, 258 |
| e | (CH$_3$)$_2$CH | (CH$_3$)$_2$CH | H | CH$_3$ | 226, 242 |
| f | H | p-NO$_2$C$_6$H$_4$ | H | CH$_3$ | 226, 318 |
| g | H | C$_6$H$_5$ | OCH$_3$ | CH$_3$ | 260, 296, 350 |
| h | H | CH$_3$(CH$_2$)3 | OCH$_3$ | CH$_3$ | 248, 316, 346 |
| i | CH$_3$ | CH$_3$(CH$_2$)3 | OCH$_3$ | CH$_3$ | 248, 318, 347 | a) Photoprecursors for deep UV photolithography

In a typical reaction, 1-(2-nitrophenyl)ethanol (XIII; $R^3$=H, $R^4$=CH$_2$) (1.8 g; 10.8 mmol) in dry toluene (50 ml) was heated to 80° C. under an inert atmosphere, at which stage phenyl isocyanate (1.4 ml; 12 mmol) was added and the mixture was stirred at 80° C. for a further 14 h. The solvent was removed by evaporation under vacuum to give a yellow oil (3.1 g), which was purified by flash chromatography on silica eluting with a mixture of chloroform and toluene (3:1). Recrystallization of the resulting solid from toluene/petroleum ether (bp 60–80° C.) (2:1) gave colourless needles of N-[1-(2-nitrophenyl)-1-ethoxycarbonyl]-N-phenylamine Ia (2.5 g; 81% yield), mp 75–75° C.

Photoprecursors Ic, If and VIII ($R^3$=H, $R^4$=CH$_3$, $R^5$=p-(C$_6$H$_4$)$_2$CH$_2$) were prepared in a similar fashion: N-[1-(2-nitrophenyl)-1-ethoxycarbonyl]-N-butylamine Ic from 1-(2-nitrophenyl)ethanol (1.71 g; 10.0 mmol) and butyl isocyanate (1.49 g; 15 mmol), as a light-yellow oil (2.0 g; 75% yield); N-[1-(2-Nitrophenyl)-1-ethoxycarbonyl]-N-(4-nitrophenyl)amine If form 1-(2-nitrophenyl)ethanol (1.0 g; 5.8 mmol) and 4-nitrophenyl isocyanate (1.0 g; 6.1 mmol) as yellow needles (ethyl acetate/ethanol 4:1, 0.75 g; 39.1% yield), mp 163–164° C.; N,N'-bis-[1-(2-Nitrophenyl)-1-ethoxycarbonyl]-4,4'-diaminodiphenyl-methane VIII ($R^3$=H, $R^4$=CH$_3$, $R^5$=p-(C$_6$H$_4$)$_2$CH$_2$) from 1-(2-nitrophenyl)ethanol (1.5 g; 9 mmol) and 4,4'-diisocyanatodiphenylmethane (MDI) (1.0 g; 4 mmol) as colourless needles (ethyl acetate, 1.98 g; 85% yield), mp 80–82° C.

N-[1-(2-Nitrophenyl)-1-ethoxycarbonyl]-N,N-diethylamine Id

Diethylamine (4 ml; 18 mmol) was added to a solution of 1-(2-nitrophenyl)-1-ethoxycarbonyl chloride (XIV; $R^3$=H, $R^4$=CH$_3$; 2.0 g; 8.7 mmol) in dichloromethane (50 ml) under an inert atmosphere and the resulting solution was refluxed for 24 hr. After addition of water (50 ml) the organic material was extracted with dichloromethane (3×30 ml) to give an oil, which was purified by flash chromatography on silica, eluting with dichloromethane, to afford the required carbamate as a light-green oil (0.9 g; 45% yield).

N-[1-(2-Nitrophenyl)-1-ethoxycarbonyl]-N,N-diisopropylamine Ie 1-(2-Nitrophenyl)-1-ethoxycarbonyl chloride (XIV; $R^3$=H, $R^4$=CH$_3$; 1.4 g; 6 mmol) was dissolved in diisopropylamine (30 ml) under an inert atmosphere and the solution was refluxed for 48 hr. The resulting diisopropylammonium chloride was filtered off and excess of diisopropylamine was removed by evaporation under vacuum to give an oil, which was purified by flash chromatography on silica, eluting with dichloromethane to afford the required compound as a colourless solid. Recrystallization from toluene-petroleum ether (bp 60–80° C.) 2:1 gave colourless crystals (1.0 g; 57% yield), mp 40–41° C.

N-[1-(2-Nitrophenyl)-1-ethoxycarbonyl]-N-methyl-N-phenylamine Ib

N-[1-(2-Nitrophenyl)-1-ethoxycarbonyl]-N-phenylamine Ia (1.0 g; 3.4 mmol) in dry dimethylformamide (10 ml) was added to a slurry of sodium hydride (80% w/w; 0.19 g; 3.5 mmol) in dry dimethylformamide (20 ml) under an inert atmosphere. The mixture was stirred at room temperature for 15 min and then methyl iodide (2.1 ml; 34.9 mmol) was added over a period of 10 min. The reaction mixture was warmed to 50° C. and stirred at this temperature for a further 30 min. The precipitate of sodium iodide was filtered off and the solvent was removed by evaporation under vacuum to give a viscous oil, which was purified by flash chromatography on silica, eluting with dichloromethane, to afford the required compound as a colourless solid. Recrystallization from toluene gave colourless crystals (0.9 g; 86% yield), mp 62–63° C.

b) Photoprecursors for UV/visible photolithography

Phenyl isocyanate (1.4 ml; 12 mmol) in toluene (5 ml) was added to a solution of 1-(4,5-dimethoxy-2-nitrophenyl)ethanol (XIII; $R^3$=OCH$_3$, $R^4$=CH$_3$) (2 g; 8.8 mmol) in dry toluene (50 ml) over a period of 10 min under an inert atmosphere. The mixture was refluxed for 24 hr, after which the solvent was removed by evaporation under vacuum to give a thick yellow oil (2.9 g; 95%); this was purified by flash chromatography on silica, eluting with chloroform, to give N-[1-(4,5-dimethoxy-2-nitrophenyl)-1-ethoxycarboxyl]-N-phenylamine Ig as a light yellow oil (2.4 g; 78.6%). In a similar way, N-[1-(4,5-dimethoxy-2-nitrophenyl)-1-ethoxycarboxyl]-N-butylamine Ih was prepared from 1-(4,5-dimethoxy-2-nitrophenyl)ethanol (1g; 4.4 mmol) and butyl isocyanate (1 ml; 5.9 mmol). Purification by flash chromatography on silica, eluting with chloroform, gave a light yellow oil, which slowly solidified. Pale yellow plates (from toluene; 1.2 g; 86.4%), 58–60° C.

Carbamate Ii was obtained from this last carbamate Ih by N-alkylation: N-[1-(4,5-dimethoxy-2-nitrophenyl)-1-ethoxycarboxyl]-N-butylamine Ih (1.0 g; 3.4 mmol) in dry dimethylformamide (10 ml) was added to a slurry of sodium hydride (80% w/w; 0.19 g; 3.5 mmol) in dry dimethylformamide (20 ml) under an inert atmosphere. The mixture was stirred at room temperature for 15 min and then methyl iodide (2.1 ml; 34.9 mmol) was added over a period of 10 min. The reaction mixture was warmed to 50° C. and stirred at this temperature for another 30 min. The resulting sodium iodide was filtered off and the solvent was removed by evaporation under vacuum to give a viscous oil. Purification by flash chromatography on silica, eluting with dichloromethane, afforded N-[1-(4,5-dimethoxy-2-nitrophenyl)-1-ethoxycarboxyl]-N-butyl-N-methylamine Ii as a light yellow oil (0.84 g; 84% yield).

c) Polymeric photoprecursors i) Polyether-urethane (IX; $R^4$=CH$_3$, $R^5$=C$_6$H$_8$, $R^6$=(CH$_2$)$_4$)

1,4-bis(3'-hydroxymethyl-4'-nitrophenoxy)butane (0.3 g; 0.76 mmol) was placed in a round-bottom flask along with pyridine (1 ml) and 1,4-diisocyamatobutane (0.1428 g; 1.44 mmol), before being left heating gently for 3 days. At this point tlc indicated that all the starting material had disappeared and a yellow glue-type substance remained. The material was insoluble in most of the general solvents, however, it was dissolved in dimethyl sulphoxide and precipitated out using ethanol. To isolate the precipitate it was necessary to use a centrifuge. The solution was allowed to spin for 30 mins, solvent was poured off, and the solid was placed in a vacuum desiccator to dry overnight. A brown coloured solid was obtained with a yield of 0.14 g.

The solid was analyzed by Gel Permeation Chromatography and the average molecular weight obtained was 7744.

ii) Polyester-urethane (X; $R^4$=CH$_3$, $R^5$=(CH$_2$)$_6$, $R^6$=(CH$_2$)$_4$)

1,3-Bis(3'- hydroxymethyl-4'-nitrophenoxycarbonyl)propane (0.14 g; 0.3 mmol) was placed in a round bottom flask along with dry pyridine (2 ml) and dry toluene (10 ml). The mixture was allowed to stir for 5 mins before the addition of 1,6-diisocyanatohexane (0.7 g; 0.3 mmol). Once added the mixture was left to stir with gentle heating for 5 days before the removal of the toluene under vacuum, resulting in a pale cream solid. The solid was washed with warm chloroform to remove any small fragments of starting material. The solid was then filtered under vacuum to give a pale cream solid with what looked like small pieces of a brown glassy solid (0.14 g).

(iii) Polyurethane (V; $R^4$=CH$_3$, $R^5$=(CH$_2$)$_6$)

5-Hydroxy-2-nitrobenzylalcohol (0.40 g; 2.33 mmol) was placed in a round bottom flask along with dry pyridine (1 ml), dry toluene (10 ml) and 1,6-diisocyanatohexane (0.39 g; 2.33 mmol). The mixture was left to stir the gentle heating for 7 days, at which point the mixture was removed from the heat and allowed to cool. A whitish precipitate was present in the reaction mixture which was filtered under vacuum and washed with toluene. The solid was dried under vacuum for approximately 15 mins before being washed with dichloromethane and filtered, further washes with water and dichloromethane were carried out, and then the solid was left to filter dry. A brown waxy solid was obtained which was coated in cream powder with a yield of 0.47 g.

Photolysis of photoprecursors in solution

N-[1-(2-nitrophenyl)-1-ethoxycarbonyl-N,N-diethylamine Id (0.067 g) was dissolved in dry, distilled tetrahydrofuran (25 ml). A portion of this $10^{-2}$ M solution (10 ml) was transferred to a quartz tube and purged with a stream of nitrogen for 15 min. The deaerated solution was irradiated with the 500W Hg(Xe) arc lamp for 60 min. Samples of irradiated and non-irradiated solutions were qualitatively analysed by GC/MS. Analysis of the chromatograms indicated photodecomposition of the carbamate and formation of N,N-diethylamine, m/z 73 [M$^+$].

In a similar way, the other carbamates were photolysed:

N-[1-(2-nitrophenyl)-1-ethoxycarbonyl-N-phenylamine Ia (0.072 g) in tetrahydrofuran (25 ml) was irradiated for 60 mins. GC/MS analysis of the solutions indicated decomposition of the starting carbamate with formation of aniline, m/z 93 [M$^+$] and 2-aminoacetophenone, m/z 135 [M$^+$].

N-[1-(2-Nitrophenyl)-1-ethoxycarbonyl-N-(4-nitrophenyl)amine If (0.083 g) in tetrahydrofuran (25 ml) was irradiated for 60 min. GC/MS analysis of the solution indicated decomposition of the starting carbamate with formation of 4-nitroaniline, m/z 138 [M$^+$] and 2-aminoacetophenone, m/z 135 [M$^+$].

Similarly, N-[1-(2-nitrophenyl)-1-ethoxycarbonyl-N-butylamine Ic (0.070 g) in methanol (25 ml) was irradiated for 60 min to form butylamine, m/z 73 [M$^+$] and 2-aminoacetophenone, m/z 135 [M$^+$]; N-[1-(2-nitrophenyl)-1-ethoxycarbonyl-N,N-diisopropylamine Ie (0.075 g) in THF (25 ml) irradiated for 60 min gave N,N-diisopropylamine, m/z 102 [M+H]$^+$ and 2-aminoacetophenone, m/z 135 [M$^+$];

N-[1-(2-Nitrophenyl)-1-ethoxycarbonyl-N-methyl-N-phenylamine Ib (0.076 g) in tetrahydrofuran (25 ml) irradiated for 60 min gave N-methyl-N-phenylamine, m/z 107 [M$^+$] and 2-aminoacetophenone, m/z 135 [M$^+$];

N-[1-(4,5-dimethoxy-2-nitrophenyl)-1-ethoxycarbonyl-N-butylamine Ih (0.080 g) in methanol (25 ml) irradiated for 60 min afforded butylamine, m/z 73 [M$^+$] and 4,5-dimethoxy-2-nitrosoacetophenone, m/z 177 [M$^+$];

N-[1-(4'-5'-dimethoxy-2-nitrophenyl)-1-ethoxycarbonyl-N-phenylamine Ig (0.072 g in tetrahydrofuran (25 ml) irradiated for 60 min gave aniline, m/z 93 [M⁺] and 4,5-dimethoxy-2-nitrosoacetophenone, m/z 177 [M⁺]; and N,N'-bis-[1-(2-nitrophenyl)-1-ethoxycarbonyl]-4,4'-diaminodiphenylmethane VIII (R³=H, R⁴=CH₃, R⁵=p-(C₆H₄)₂CH₂) (0.15 g) in tetrahydrofuran (25 ml) gave bis(4-aminophenyl)methane, m/z 199 [M+H]⁺, 2-nitrosoacetophenone, m/z 150 [M+H]⁺, 2-aminoacetophenone, m/z 135 [M⁺] and 2-nitroacetophenone, m/z 166 [M+H]⁺.

Preparation of lithographic printing plates

A polymeric amine photoprecursor (IX; R⁴=CH₃, R⁵=C₄H₈, R⁶(CH₂)₄) (0.25 g) was dissolved in dimethylformamide (25 ml) and polyvinylpyridine (0.25 g) was added, together with Bromothymol Blue (0.02 g). The resulting solution was stirred and filtered. Separate sheets of grained and anodised aluminium were independently treated with aqueous solutions containing either (a) 4.5% w/w potassium fluorotitanate or (b) 2.% w/w polyvinylphosphonic acid. Samples of the two treated aluminium sheets were coated with the solution containing photoprecursor, and the resulting printing plate precursors were baked in an oven at 100° C. for two minutes.

Samples of the printing plate precursors were then exposed through a 21-step grey-scale Stouffer step wedge in a Berkey Ascor printing-down frame delivering 406 mJ/cm² to give a pronounced yellow to blue colour change and leave an image in each case. Two samples of each of the plate precursors were then developed with aqueous developers containing either (a) 5% w/w phosphoric acid and 10% w/w Dowfax 2A1 (anionic surfactant) or (b) 5% Pelex (sulphonated naphthalic acid) and 3% benzyl alcohol to provide positive-working and negative-working images, respectively, of the Stouffer step wedge. Hand inking of the plates showed the images to be highly oleophilic and gave step wedge readings of clear 3 in the former case and solid 4 with the latter plate. When placed on a web offset press, clean copies were immediately produced in each case.

What is claimed is:

1. A method of preparation of photoprecursors comprising the steps of:

(a) nitrating an aromatic aldehyde or ketone XI to provide the o-nitro derivative XII;

(b) reducing said o-nitro derivative XII to the corresponding alcohol XIII; and (c) reacting said alcohol XIII with mono- or diisocyanates to provide 2-nitrobenzyl urethane derivatives I or VIII as follows:

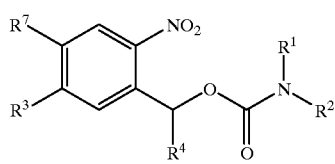

wherein R² = H

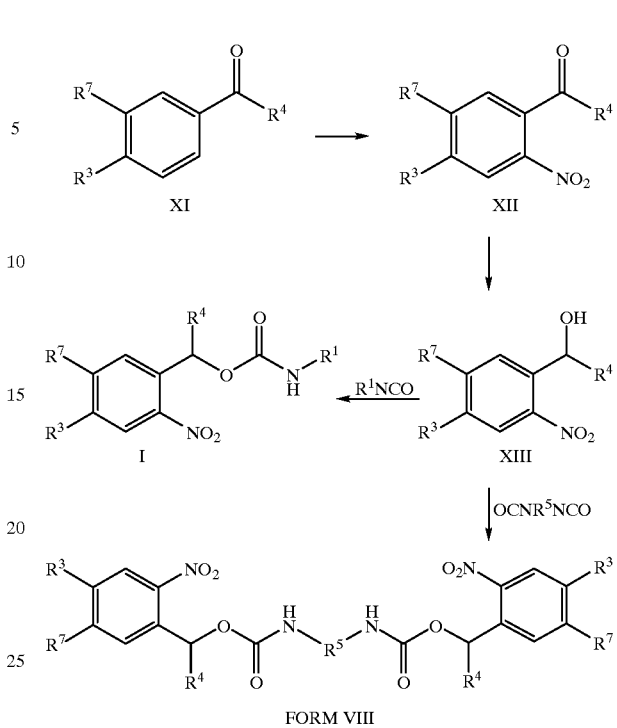

FORM VIII

R¹ = H or optionally substituted alkyl, aryl or aralkyl;
R³, R⁷ = H or an electron donating group;
R⁴ = H or lower alkyl;
R⁵ = optionally substituted alkylene, arylene or aralkylene.

2. A method as defined in claim 1 wherein said ketone is selected from acetophenone or 3,4-dimethoxyacetophenone.

3. A method as defined in claim 1 wherein said mono- or di-isocyanate is selected from butyl isocyanate, hexane-6,6-diisocyanate, phenyl isocyanate, 4,4'-diisocyanatodiphenylmethane or 4-nitrophenylisocyanate.

4. A method as defined in claim 1 wherein said aldehyde or ketone is selected from a bisaldehyde or bisketone, said mono- or di-isocyanate comprises a di-isocyanate, and said photoprecursor comprises a polymeric photoprecursor.

5. A method of preparation of photoprecursors comprising the steps of:

(a) nitrating an aromatic aldehyde or ketone XI to provide the o-nitro derivative XII;

(b) reducing said o-nitro derivative XII to the corresponding alcohol XIII;

(c) reacting said alcohol XIII with carbonyl chloride to provide the corresponding chlorocarbonate XIV; and (d) condensing said chlorocarbonate XIV with a secondary amine to provide 2-nitrobenzyl urethane derivatives I

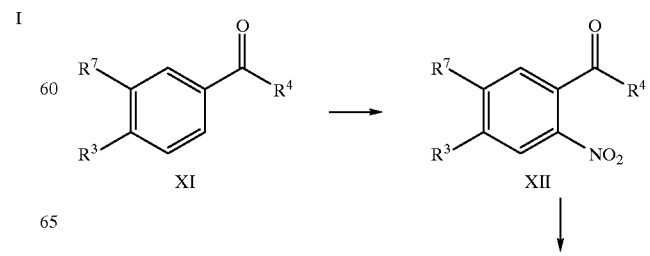

-continued

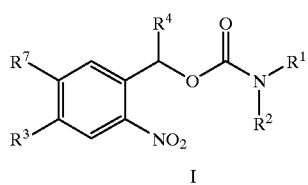

I

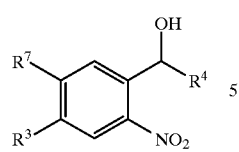

XIII

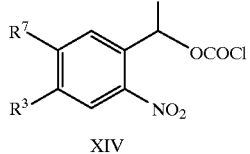

XIV $R^1, R^2$ = H or optionally substituted alkyl, aryl or aralkyl;
$R^3, R^7$ = H or an electron donating group;
$R^4$ = H or lower alkyl.

6. A method as defined in claim 5 wherein said ketone is selected from acetophenone or 3,4-dimethoxyacetophenone.

7. A method as defined in claim 5 wherein said secondary amine is selected from an optionally substituted dialkylamine.

8. A method as defined in claim 7 wherein said dialkylamine is selected from diethylamine or diisopropylamine.

9. A method as described in claim 1 wherein said electron donating group is an alkyl or an alkoxy.

10. A method as defined in claim 5 wherein said electron donating group is an alkyl or an alkoxy.

* * * * *